United States Patent [19]
Lassila et al.

[11] Patent Number: 5,985,968
[45] Date of Patent: Nov. 16, 1999

[54] SURFACE TENSION REDUCTION WITH N, N-DIALKYL UREAS

[75] Inventors: Kevin Rodney Lassila, Macungie; John Anthony Marsella, Allentown, both of Pa.

[73] Assignee: Air Products and Chemicals, Inc., Allentown, Pa.

[21] Appl. No.: 08/972,075

[22] Filed: Nov. 17, 1997

[51] Int. Cl.[6] .................................................. C08K 5/21
[52] U.S. Cl. ..................... 524/211; 252/521; 510/128; 524/215; 564/32; 564/58; 564/63
[58] Field of Search .................. 564/32, 58, 63; 524/211, 215; 252/321; 510/128

[56] References Cited

U.S. PATENT DOCUMENTS

| | | | |
|---|---|---|---|
| 2,335,862 | 12/1943 | Klingel | 514/70 |
| 2,374,187 | 4/1945 | Flett | 252/152 |
| 2,708,183 | 5/1955 | Ross | 252/137 |
| 3,691,082 | 9/1972 | Stimberg et al. | 252/98 |
| 3,814,705 | 6/1974 | Inamorato et al. | 252/525 |
| 3,965,015 | 6/1976 | Bauman | 252/8.8 |
| 4,272,413 | 6/1981 | Bauman | 252/544 |
| 4,310,692 | 1/1982 | Findeisen et al. | 564/61 |
| 4,460,727 | 7/1984 | Shoji | 524/215 |
| 5,039,759 | 8/1991 | Hoy et al. | 525/437 |
| 5,098,478 | 3/1992 | Krishnan et al. | 106/23 |
| 5,118,344 | 6/1992 | Nguyen | 252/390 |
| 5,562,762 | 10/1996 | Mrvos et al. | 106/22 H |

FOREIGN PATENT DOCUMENTS

| | | |
|---|---|---|
| 492817 | 5/1953 | Canada . |
| 4341984 | of 0000 | Germany . |

OTHER PUBLICATIONS

Kosswig, Ullmann's Encyclopedia of Industrial Chemistry, Fifth Edition, Vol. A25, VCH, 1994.

Medina, S. W.; Sutovich, M.N., "Using Surfactants to Formulate VOC Compliant Waterbased Inks" Am.Ink Maker 1994, 72 (2), 32–38.

Wirth, W.; Storp, S.; Jacobsen, W. "Mechanisms Controlling Leaf Retention of Agricultural Spray Solutions", Pestic. Sci. 1991,33, 411–420.

Schwartz, J., "The Importance of Low Dynamic Surface Tension in Waterborne Coatings" Journal of Coatings Technology, Sep. 1992.

Mysels, K.J., "Improvements in the Maximum–Bubble–Pressure Method of Measuring Surface Tension", American Chemical Society, 1986 pp. 428–432.

*Primary Examiner*—David W. Wu
*Assistant Examiner*—Ling-Siu Choi
*Attorney, Agent, or Firm*—Michael Leach

[57] ABSTRACT

This invention provides water-based compositions, particularly coating, ink, and agricultural compositions, manifesting reduced equilibrium and dynamic surface tension by the incorporation of an effective amount of certain N,N-dialkyl urea compounds of the structure

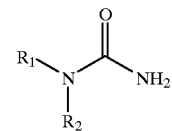

where R and R' are independently C1 to C6 alkyl or cycloalkyl with the sum of the carbon atoms in both $R_1$ and $R_2$ being 6 to 12.

16 Claims, No Drawings

SURFACE TENSION REDUCTION WITH N, N-DIALKYL UREAS

FIELD OF THE INVENTION

The invention relates to the use of N,N-dialkyl ureas to reduce the surface tension in water-based systems.

BACKGROUND OF THE INVENTION

The ability to reduce the surface tension of water is of great importance in waterborne coatings, inks, adhesives, and agricultural formulations because decreased surface tension translates to enhanced substrate wetting in actual formulations. Surface tension reduction in water-based systems is generally achieved through the addition of surfactants. Performance attributes resulting from the addition of surfactants include enhanced surface coverage, fewer defects, and more uniform distribution. Equilibrium surface tension performance is important when the system is at rest. However, the ability to reduce surface tension under dynamic conditions is of great importance in applications where high surface creation rates are utilized. Such applications include spraying of coatings or agricultural formulations, or high speed gravure or ink-jet printing. Dynamic surface tension is a fundamental quantity which provides a measure of the ability of a surfactant to reduce surface tension and provide wetting under such high speed application conditions.

Traditional nonionic surfactants such as alkylphenol or alcohol ethoxylates, and ethylene oxide (EO) propylene oxide (PO) copolymers have excellent equilibrium surface tension performance but are generally characterized as having poor dynamic surface tension reduction. In contrast, certain anionic surfactants such as sodium dialkyl sulfosuccinates can provide good dynamic results, but these are very foamy and impart water sensitivity to the finished coating.

The objective of this invention is to provide a family of surfactants which provide good equilibrium and dynamic surface tension properties and are low-foaming.

The importance of reducing equilibrium and dynamic surface tension in applications such as coatings, inks, and agricultural formulations is well-appreciated in the art.

Low dynamic surface tension is of great importance in the application of waterborne coatings. In an article, [Schwartz, J. *"The Importance of Low Dynamic Surface Tension in Waterborne Coatings"*, Journal of Coatings Technology, September 1992] there is a discussion of surface tension properties in waterborne coatings and a discussion of dynamic surface tension in such coatings. Equilibrium and dynamic surface tension were evaluated for several surface active agents including the ethylene oxide adducts of acetylenic glycols. It is pointed out that low dynamic surface tension is an important factor in achieving superior film formation in waterborne coatings. Dynamic coating application methods require surfactants with low dynamic surface tensions in order to prevent defects such as retraction, craters, and foam.

Efficient application of agricultural products is also highly dependent on the dynamic surface tension properties of the formulation. In an article, [Wirth, W.; Storp, S.; Jacobsen, W. *"Mechanisms Controlling Leaf Retention of Agricultural Spray Solutions"*; Pestic. Sci. 1991, 33, 411–420], the relationship between the dynamic surface tension of agricultural formulations and the ability of these formulations to be retained on a leaf was studied. These workers observed a good correlation between retention values and dynamic surface tension, with more effective retention of formulations exhibiting low dynamic surface tension.

Low dynamic surface tension is also important in high-speed printing as discussed in the article *"Using Surfactants to Formulate VOC Compliant Waterbased Inks"* [Medina, S. W.; Sutovich, M. N. Am. Ink Maker 1994, 72 (2), 32–38]. In this article, it is stated that equilibrium surface tensions (EST's) are pertinent only to ink systems at rest. EST values, however, are not good indicators of performance in the dynamic, high speed printing environment under which the ink is used. Dynamic surface tension is a more appropriate property. This dynamic measurement is an indicator of the ability of the surfactant to migrate to a newly created ink/substrate interface to provide wetting during high speed printing.

U.S. Pat. No. 5,098,478 discloses water-based ink compositions comprising water, a pigment, a nonionic surfactant and a solubilizing agent for the nonionic surfactant. Dynamic surface tension in ink compositions for publication gravure printing must be reduced to a level of about 25 to 40 dynes/cm to assure that printability problems will not be encountered.

U.S. Pat. No. 5,562,762 discloses an aqueous jet ink of water, dissolved dyes and a tertiary amine having two polyethoxylate substituents and that low dynamic surface tension is important in ink jet printing.

U.S. Pat. No. 3,814,705 discloses the use of long chain 1,1-dialkyl ureas of the type R2NC(O)NH2 (R=alkyl group of C8 to C18) as foam suppressants in detergent compositions containing organic detergents, such as sulfate and sulfonate detergents, and alkaline builder salts.

Similarly, U.S. Pat. No. 3,691,082 discloses low-foaming rinsing, washing and cleaning compositions comprising (a) at least one compound having a cleaning or complexing action, (b) a foam-inhibiting isocyanurate and (c) an alkylated urea having at least eight substituents carbons on each of the urea nitrogens.

U.S. Pat. No. 2,708,183 discloses synthetic detergent compositions comprising a sulfated or sulfonated detergent and a minor amount of a higher alkyl substituted urea characterized by limited water-solubility.

U.S. Pat. No. 2,374,187 discloses non-allergenic toilet bars comprising sulfonated detergents and water-soluble, solid organic compounds which contain within the molecule the carboacylamido radical, e.g., ureas. The ureas are a significant amount of the final composition (50–95%).

U.S. Pat. No. 3,965,015 discloses bleach-stable fabric detergent and/or softening compositions comprising effective amounts of a urea represented by the formula: RNHCXNH(CH2)nNH2 where R is a C2–C18 alkyl group, X is oxygen or sulfur and n is 2–12.

U.S. Pat. No. 4,272,413 discloses softening and antistatic laundering compositions compatible with detergents comprising as the softening and antistatic agents short chain carbamoyl derivatives of long chain aliphatic amines, where the amino nitrogen is attached to a non-terminal or internal methylene group.

U.S. Pat. No. 2,335,862 discloses N,N-dibutylurea as a good solvent for rotenone in a non-aqueous herbicidal application.

SUMMARY OF THE INVENTION

This invention provides water-based compositions containing an organic compound, particularly organic coating, ink, and agricultural compositions, having reduced equilibrium and dynamic surface tension by incorporation of an effective amount of certain N,N-dialkyl urea compounds of the structure

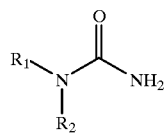

where $R_1$ and $R_2$ are independently C1 to C6 alkyl or cycloalkyl with the sum of carbon atoms in both R and R' being 6 to 12.

Also provided is a method for applying a water-based composition to a surface, the composition containing an effective amount of an N,N-dialkyl urea compound of the above structure for reducing the dynamic surface tension of the composition.

There are significant advantages associated with the use of these N,N-dialkyl urea compounds in water-based organic coatings, inks, and agricultural compositions and these advantages include:

an ability to formulate water-borne coatings, inks, and agricultural compositions which may be applied to a variety of substrates with excellent wetting of substrate surfaces including contaminated and low energy surfaces;

an ability to provide a reduction in coating or printing defects such as orange peel and flow/leveling deficiencies;

an ability to produce water-borne coatings and inks which have low volatile organic content, thus making these surfactants environmentally favorable;

an ability to formulate coating and ink compositions capable of high speed application;

Because of their excellent surfactant properties and low foam characteristics, these materials are likely to find applicability in many applications in which reduction in dynamic and equilibrium surface tension and low foam are important. Such applications include various wet-processing textile operations, such as dyeing of fibers, fiber souring, and kier boiling, where low-foaming properties would be particularly advantageous; they may also have applicability in soaps, water-based perfumes, shampoos, and various detergents where their marked ability to lower surface tension and at the same time produce substantially no foam would be highly desirable.

DETAILED DESCRIPTION OF THE INVENTION

This invention relates to the use of compounds of the formula

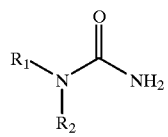

where $R_1$ and $R_2$ are independently C1 to C6 alkyl or cycloalkyl with the total number of carbons in R and R' being 6–12 for the reduction of equilibrium and dynamic surface tension in water-based formulations containing an organic compound, particularly coating, ink, and agricultural formulations. It is desirable that an aqueous solution of the N,N-dialkyl urea demonstrates a dynamic surface tension of less than 45 dynes/cm at a concentration of $\leq 5$ wt % in water at 23° C. and 1 bubble/second according to the maximum-bubble-pressure method. The maximum-bubble-pressure method of measuring surface tension is described in *Langmuir* 1986, 2, 428–432, which is incorporated by reference.

These N,N-dialkyl ureas can be prepared by the reaction of an appropriate dialkylamine with an alkali metal cyanate in the presence of acid. This reaction is illustrated using potassium cyanate a nd hydrochloric acid:

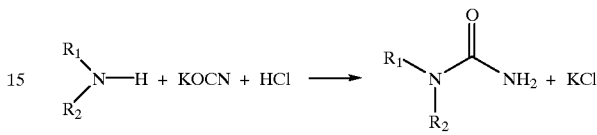

Alternatively, the compounds may be prepared by reaction of urea with an dappropriate dialkylamine:

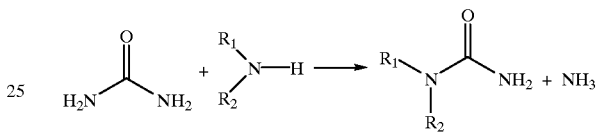

For commercial production, the latter method would be preferred.

Any secondary amine containing the requisite C1 to C6 alkyl substituents may be utilized for the preparation of the compounds of this invention. Alkyl groups which are suitable should have sufficient carbon to confer surface activity (i.e. an ability to reduce the surface tension of water) to the material but not enough carbon to decrease the solubility to the extent that the ability of the material to reduce surface tension is insufficient for a particular application. In general, an increase in the carbon number increases the efficiency of the resulting urea surfactant (i.e., less surfactant is required to obtain a given decrease in surface tension) but decreases its ability to reduce surface tension at high surface creation rates (i.e., less effective for reducing dynamic surface tension). The latter effect is a result of the fact that increased carbon number generally decreases the water solubility of the material, and consequently, diminishes the diffusive flux of surfactant to newly-created surface. Generally, in the practice of this invention, it is desirable to choose alkyl groups such that the resulting dialkylureas have a solubility in water of at least 0.005 wt %, preferably from 0.01 to 2 wt %, and most preferably from 0.1 to 1.5 wt %.

The alkyl groups may be the same or different. They may be linear or branched, and the point of attachment to the nitrogen may be on either an internal or terminal carbon. The total number of carbons on the alkyl substituents should be at least 6; fewer than this diminishes the surface activity of the urea too greatly. The total number of carbons should be no greater than 12; a greater number decreases the solubility of the material to such a degree that its use in many formulations is impractical. Examples of suitable alkyl groups are methyl, ethyl, n-propyl, isopropyl, n-butyl, isobutyl, sec-butyl, n-pentyl, 2-pentyl, 3-pentyl, isopentyl, n-hexyl, 2-hexyl, 3-hexyl, cyclohexyl, and the like. Preferred derivatives contain 8 to 10 alkyl carbons. The alkyl carbons may be distributed among the alkyl substituents in any manner, although derivatives in which the alkyl groups contain equivalent numbers of carbons are preferred because parent amines of this type are most economical and readily available.

An amount of the dialkyl urea compound that is effective to reduce the equilibrium and/or dynamic surface tension of the water-based, organic compound-containing composition is added. Such effective amount may range from 0.001 to 20 g/100 ml, preferably 0.01 to 2 g/100 ml, of the aqueous composition. Naturally, the most effective amount will depend on the particular application and the solubility of the N,N-dialkyl urea.

In the following water-based organic coating, ink, and agricultural compositions containing a dialkylurea according to the invention, the other listed components of such compositions are those materials well known to the workers in the relevant art.

A typical water-based organic coating composition to which the dialkylurea surfactants of the invention may be added would comprise the following components in an aqueous medium at 30 to 80% solids:

| Typical Water-Based Organic Coating Composition | |
|---|---|
| 0 to 50 wt % | Pigment Dispersant/Grind Resin |
| 0 to 80 wt % | Coloring Pigments/Extender Pigments/Anti-Corrosive Pigments/Other Pigment Types |
| 5 to 99.9 wt % | Water-Borne/Water-Dispersible/Water-Soluble Resins |
| 0 to 30 wt % | Slip Additives/Antimicrobials/Processing Aids/Defoamers |
| 0 to 50 wt % | Coalescing or Other Solvents |
| 0.01 to 10 wt % | Surfactant/Wetting Agent/Flow and Leveling Agents |
| 0.01 to 5 wt % | N,N-Dialkyl urea |

A typical water-based ink composition to which the dialkylurea surfactants of the invention may be added would comprise the following components in an aqueous medium at 20 to 60% solids:

| Typical Water-Based Ink Composition | |
|---|---|
| 1–50 wt % | Pigment |
| 0 to 50 wt % | Pigment Dispersant/Grind Resin |
| 0–50 wt % | Clay base in appropriate resin solution vehicle |
| 5 to 99.9 wt % | Water-Borne/Water-Dispersible/Water-Soluble Resins |
| 0–30 wt % | Coalescing Solvents |
| 0.01 to 10 wt % | Surfactant/Wetting Agent |
| 0.01 to 10 wt % | Processing Aids/Defoamers/Solubilizing Agents |
| 0.01 to 5 wt % | N,N-Dialkyl urea |

A typical water-based agricultural composition to which the dialkylurea surfactants of the invention may be added would comprise the following components in an aqueous medium at 0.1 to 80% ingredients:

| Typical Water-Based Agricultural Composition | |
|---|---|
| 0.1 to 50 wt % | Pesticide or Plant Growth Modifying Agent |
| 0.01 to 10 wt % | Surfactant |
| 0 to 5 wt % | Dyes |
| 0 to 20 wt % | Thickeners/Stabilizers/Co-surfactants/Gel Inhibitors/Defoamers |
| 0 to 25 wt % | Antifreeze |
| 0.1 to 50 wt % | N,N-Dialkyl urea |

EXAMPLE 1

This example illustrates the preparation of N,N-dibutylurea. Di-n-butylamine (56.9 g) was mixed with 300 mL ice water and neutralized with about 76 mL 5 M HCl. Neutralization was confirmed by measuring the pH and adjusting as needed with HCl or dibutylamine to give a pH of 7. The solution was heated to about 80° C. and 35.7 g potassium cyanate was added in one to five gram portions. An organic layer formed after a few minutes and heating was continued at 80° C. for two hours. The organic layer was dissolved in a minimum of toluene and dried over anhydrous magnesium sulfate. The toluene was removed on a rotary evaporator to give 61.5 g (81% yield) of a clear colorless oil.

EXAMPLE 2

This example illustrates the preparation of N,N-dihexylurea. This material was synthesized in a manner similar to that of Example 1 using di-n-hexylamine and potassium cyanate, except that a 25% excess of potassium cyanate was used and methanol was required to dissolve a solid hydrate that formed on addition of water to di-n-hexylamine. Yield: 89%.

Other dialkyl ureas were prepared similarly. Some of the more water soluble products had to be extracted with toluene from the aqueous solution at the end of the reaction.

In the following examples dynamic surface tension data were generated for aqueous solutions of the indicated compounds using the maximum-bubble-pressure method at the indicated bubble rates, i.e., bubbles/second (b/s), and room temperature of about 23° C. The equipment used was a Krüss BP 2 bubble pressure tensiometer.

COMPARATIVE EXAMPLE 3

A series of aqueous solutions of various concentrations of n-octylurea [Pfaltz & Bauer] was prepared by placing the urea into water and shaking the mixture for 1–2 h. All of the urea dissolved in the low concentration samples. Undissolved urea in some of the higher concentration samples was remove by filtration. Surface tensions of these solutions were measured using the Wilheimy plate technique. This method provides equilibrium surface tension values. Equilibrium values are always equal to or lower than those obtained under dynamic conditions. The data are set forth in Table 1.

TABLE 1

| N-Octylurea | |
|---|---|
| Conc (wt %) | dyne/cm |
| 0.0001 | 72.2 |
| 0.0005 | 72.1 |
| 0.001 | 72.0 |
| 0.003 | 68.9 |
| 0.005 | 62.4 |
| 0.007 | 60.0 |
| 0.009 | 57.0 |
| 0.015 | 57.1 |
| 0.03 | 55.5 |
| 0.06 | 57.1 |

These data indicate that the lowest surface tension which can be obtained for an aqueous solution of n-octylurea is about 56 dyne/cm and that the solubility limit is 0.01 wt %. Because of the high limiting surface tension, this compound would not be useful as a surface tension reducing agent.

COMPARATIVE EXAMPLE 4

A saturated solution in distilled water of N,N'-di-n-butylurea was prepared by placing 0.1 g of the urea into 99.9 g of water and shaking the mixture for 1–2 h. Most of the N,N'-di-n-butylurea remained undissolved. The solids were removed by filtration, and the dynamic surface tension of the resulting solution was measured using the maximum bubble pressure method at bubble rates from 0.1 to 20 b/s. These data provide information about the performance of a surfactant at conditions from near-equilibrium (0.1 b/s) through extremely high surface creation rates (20 b/s). In practical terms, high bubble rates correspond to high printing speeds in lithographic or ink-jet printing, high spray or roller velocities in coating applications, and rapid application rates for agricultural products. The data are set forth in Table 2.

TABLE 2

N,N'-Di-n-butylurea.

| Concentration | Dynamic Surface Tension (dyne/cm) | | | | |
|---|---|---|---|---|---|
| | 0.1 b/s | 1 b/s | 6 b/s | 15 b/s | 20 b/s |
| saturated (<0.1 wt %) | 59.0 | 59.6 | 60.2 | 60.6 | 60.9 |

The high limiting surface tension of this compound indicates it would not be useful as a surface tension reducing agent.

EXAMPLE 5

Aqueous solutions of N,N-dibutylurea were prepared and their surface tensions were measured using the procedure described above. The data are set forth in Table 3.

TABLE 3

N,N-Dibutylurea.

| Concentration | Dynamic Surface Tension (dyne/cm) | | | | |
|---|---|---|---|---|---|
| (wt %) | 0.1 b/s | 1 b/s | 6 b/s | 15 b/s | 20 b/s |
| 0.3 | 42.9 | 43.1 | 43.4 | 43.4 | 43.6 |
| 1.0 | 32.7 | 32.9 | 33.2 | 33.8 | 34.1 |
| 1.5 | 28.2 | 28.3 | 28.5 | 29.1 | 29.5 |

These results show that N,N-dibutylurea is highly effective at reducing the surface tension of water. This is unanticipated in view of the fact that other urea derivatives containing eight alkyl carbons are so ineffective at lowering surface tension, as shown in Comparative Examples 3 and 4. At a use level of 1.5 wt %, the surface tension remained below 30 dyne/cm even at the extremely high surface creation rate of 20 b/s. The enhanced performance at high surface creation rates could be extremely important in formulating water-based coating, ink, and agricultural products for high speed applications, particularly for low energy surfaces.

EXAMPLE 6

N,N-dipentylurea was prepared using the procedure of Example 1 using a dipentyl amine mixture which contained isomeric pentyl groups derived from fusel oil or another C5 byproduct stream. Aqueous solutions of the resulting N,N-dipentylurea were prepared and their surface tensions were measured using the procedure described above. The data are set forth in Table 4.

TABLE 4

N,N-Dipentylurea.

| Concentration | Dynamic Surface Tension (dyne/cm) | | | | |
|---|---|---|---|---|---|
| (wt %) | 0.1 b/s | 1 b/s | 6 b/s | 15 b/s | 20 b/s |
| 0.1 | 36.3 | 37.1 | 38.7 | 40.7 | 41.3 |
| 0.2 | 32.8 | 33.4 | 34.6 | 36.2 | 36.3 |
| 0.3 | 30.9 | 31.5 | 32.4 | 32.9 | 33.1 |

These results show that at a concentration of 0.1 wt %, the surface tension at 0.1 b/s is 36.3 dyne/cm. The solubility limit of dipentylurea, however, is 0.3 wt %. This means that if a surface tension lower than that attainable with a 0.1 wt % solution is required for a specific application, additional dipentylurea can be added to the formulation; at a concentration of 0.3 wt %, the surface tension is 30.9 dyne/cm. At 20 b/s, the surface tension of a 0.3 wt % solution of dipentylurea is 33.1 dyne/cm. The enhanced performance at these high surface creation rates could be extremely important in obtaining high printing speeds or application rates for water-based coating, ink, and agricultural formulations.

COMPARATIVE EXAMPLE 7

A saturated solution in distilled water of N,N-di-(2-ethylhexyl)urea was prepared by placing 0.1 g of the urea into 99.9 g of water and shaking the mixture for 1–2 h. Most of the urea remained undissolved. The solids were removed by filtration, and the surface tension of the resulting solution was measured as described above. The data are set forth in Table 5.

TABLE 5

N,N-Di-(2-ethylhexyl)urea.

| Concentration | Dynamic Surface Tension (dyne/cm) | | | | |
|---|---|---|---|---|---|
| (wt %) | 0.1 b/s | 1 b/s | 6 b/s | 15 b/s | 20 b/s |
| saturated (<0.1) | 60.1 | 69.2 | 69.6 | 69.3 | 68.1 |

Similarly, a saturated solution in distilled water of N,N-di-n-octylurea was prepared by placing 0.1 g of the urea into 99.9 g of water and shaking the mixture for 1–2 hr. Most of the urea remained undissolved. The solids were removed by filtration, and the surface tension of the resulting solution was measured as described above. The data are set forth in Table 6.

TABLE 6

N,N-Di-n-octylurea.

| Concentration | Dynamic Surface Tension (dyne/cm) | | | | |
|---|---|---|---|---|---|
| (wt %) | 0.1 b/s | 1 b/s | 6 b/s | 15 b/s | 20 b/s |
| saturated (<0.1) | 52.9 | 69.8 | 71.1 | 70.3 | 69.4 |

The results show that these materials are surface active, but their low solubilities result in surface tensions nearly equal to that of water at surface-creation rates corresponding to greater than about 1 bubbles/second. Even at the low surface creation rate of 0.1 b/s, the surface tensions are still over 50 dyne/cm.

These data indicate that these compounds will have limitations with respect to their applicability in coatings, inks, adhesives, and agricultural formulations because of their poor performance under dynamic conditions.

EXAMPLE 8

A saturated solution in distilled water of N,N-di-n-hexylurea was prepared by placing 0.1 g of the urea into 99.9 g of water and shaking the mixture for 1–2 h. Most of the N,N-di-n-hexylurea remained undissolved. The solids were removed by filtration, and the surface tension of the resulting solution was measured as described above. The data are set forth in Table 7.

TABLE 7

| | N,N-Di-n-hexylurea. | | | | |
|---|---|---|---|---|---|
| Concentration | Dynamic Surface Tension (dyne/cm) | | | | |
| (wt %) | 0.1 b/s | 1 b/s | 6 b/s | 15 b/s | 20 b/s |
| saturated (<0.1) | 34.7 | 42.8 | 56.8 | 63.7 | 62.4 |

These results indicate that this material is effective at reducing the surface tension of aqueous formulations under conditions in which surface creation rates are relatively low. Because of its ability to cause a significant reduction in surface tension, this material would be expected to have significantly wider applicability than either the di-(2-ethylhexyl)urea or di-n-octylurea of the previous example.

EXAMPLE 9

Aqueous solutions of N,N-di-n-propylurea were prepared and their surface tensions were measured using the procedure described above. The data are set forth in Table 8.

TABLE 8

| | N,N-Di-n-propylurea. | | | | |
|---|---|---|---|---|---|
| Concentration | Dynamic Surface Tension (dyne/cm) | | | | |
| (wt %) | 0.1 b/s | 1 b/s | 6 b/s | 15 b/s | 20 b/s |
| 0.5 | 53.8 | 54.0 | 54.3 | 53.8 | 53.7 |
| 2.0 | 43.4 | 43.6 | 43.9 | 44.4 | 44.5 |
| 4.0 | 39.0 | 39.1 | 39.3 | 39.5 | 39.6 |

These results show that N,N-di-n-propylurea is reasonably effective at reducing the surface tension of water. In particular, it exhibits an ability to reduce the surface tension of water at high bubble rates. It would therefore be suitable for many applications for which surface tension reduction at high surface creation rates is important.

EXAMPLE 10

Aqueous solutions of N-cyclohexyl-N-methylurea were prepared and their surface tensions were measured using the procedure described above. The data are set forth in Table 9.

TABLE 9

| | N-cyclohexyl-N-methylurea. | | | | |
|---|---|---|---|---|---|
| Concentration | Dynamic Surface Tension (dyne/cm) | | | | |
| (wt %) | 0.1 b/s | 1 b/s | 6 b/s | 15 b/s | 20 b/s |
| 1.0 | 51.9 | 52.4 | 52.9 | 53.2 | 53.2 |
| 2.5 | 44.1 | 44.6 | 45.1 | 45.6 | 45.8 |

These results show that N-cyclohexyl-N-methylurea is reasonably effective at reducing the surface tension of water and that it would be suitable for many applications, particularly those which require reduction of surface tension at high surface creation rates.

EXAMPLE 11

The foaming properties of a 0.1 wt % solution of N,N-dibutylurea, N,N-dipentyl-urea, and N,N-dihexylurea were examined using a procedure based upon ASTM D 1173-53. In this test, a 0.1 wt % solution of the surfactant is added from an elevated foam pipette to a foam receiver containing the same solution. The foam height is measured at the completion of the addition ("Initial Foam Height") and the time required for the foam to dissipate is recorded ("Time to 0 Foam"). This test provides a comparison between the foaming characteristics of various surfactant solutions. In general, in coatings, inks, and agricultural formulations, foam is undesirable because is complicates handling and can lead to coating and print defects, and to inefficient application of agricultural materials.

TABLE 10

| Compound | Initial Foam Height (cm) | Time to 0 Foam |
|---|---|---|
| N,N-Dibutylurea | 3.0 | 5 s |
| N,N-Dipentyurea | 1.5 | 3 s |
| N,N-Dihexylurea | 1.0 | 2 s |

The results are reported in Table 10 and show that the compounds of this invention form a quantity of foam which dissipates quickly. Thus these materials have desirable properties with respect to their use in coatings, inks and agricultural formulations.

The ability of a surfactant in aqueous systems to reduce surface tension under both equilibrium and dynamic conditions is of great importance in the performance of water-based coatings, inks, adhesives, and agricultural formulations. Low equilibrium surface tension allows the development of excellent properties subsequent to application. Low dynamic surface tension results in enhanced wetting and spreading under the dynamic conditions of application, resulting in more efficient use of the formulations and fewer defects. In waterborne coatings, inks, adhesives, and agricultural formulations, the formation of foam is generally undesirable because it complicates handling and can cause defects or result in inefficient application.

The family of surfactants disclosed in this invention surprisingly exhibits an ability to reduce dynamic surface tension and contributes little foam to the formulations.

That N,N-dialkylureas would exhibit surface activity would not be anticipated based on the teachings of the prior art. Although ureas have been studied extensively in detergent applications, their role appears to have been to act as adjuncts to conventional detergents and not as surfactants themselves. In particular, surfactancy by relatively short chains is not apparent from the prior art. A property which is particularly not apparent from the prior art is the outstanding dynamic properties shown by ureas in reducing the surface tension of aqueous mixtures under conditions of surface creation rates.

STATEMENT OF INDUSTRIAL APPLICATION

The invention provides material suitable for reducing the equilibrium and dynamic surface tension in water-based compositions.

We claim:

1. In a method for applying a water-based composition to a surface, the composition containing an effective amount of a surfactant for reducing the dynamic surface tension of the composition, the improvement which comprises employing as the surfactant, at 0.001 to 20 g/100 ml of the water-based composition, an N,N-dialkyl urea compound of the structure

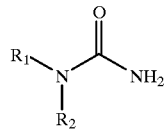

where $R_1$ and $R_2$ are independently C1 to C6 alkyl or cycloalkyl, the sum of the carbon atoms in both $R_1$ and $R_2$ being 6 to 12, provided that when the urea compound is N,N-dibutyl urea, the amount is 0.01 to 2 g /100 ml.

2. The method of claim 1 in which an aqueous solution of the N,N-dialkyl urea demonstrates a dynamic surface tension of less than 45 dynes/cm at a concentration of ≦5 wt % in water at 23° C. and 1 bubble/second according to the maximum-bubble-pressure method.

3. The method of claim 1 in which the carbon atoms total 8 to 10.

4. The method of claim 1 in which the urea is N,N-dibutyl urea.

5. The method of claim 1 in which the urea is N,N-dipentyl urea.

6. The method of claim 1 in which the urea is N,N-dihexyl urea.

7. The method of claim 2 in which the measurement is made at 20 bubbles/second.

8. An aqueous composition comprising an organic compound and 0.001 to 20 g/100 ml of the aqueous composition of an N,N-dialkyl urea for reducing the dynamic surface tension of the composition, the N,N-dialkyl urea compound having the structure

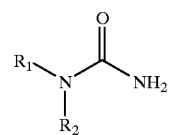

where $R_1$ and $R_2$ are independently C1 to C6 alkyl or cycloalkyl, the sum of the carbon atoms in both $R_1$ and $R_2$ being 6 to 12, provided that when the urea compound is N,N-dibutyl urea, the amount is 0.01 to 2 g/100 ml.

9. The composition of claim 8 in which an aqueous solution of the N,N-dialkyl urea demonstrates a dynamic surface tension of less than 45 dynes/cm at a concentration of ≦5 wt % in water at 23° C. and 1 bubble/second according to the maximum-bubble-pressure method.

10. The composition of claim 8 in which the urea is N,N-dibutyl urea.

11. The composition of claim 8 in which the urea is N,N-dipentyl urea.

12. The composition of claim 8 in which the urea is N,N-dihexyl urea.

13. The composition of claim 8 in which the aqueous composition is an organic coating, ink, or agricultural composition.

14. The composition of claim 8 which is an organic coating composition of 30 to 80 wt % components, which components comprise 0 to 50 wt % pigment dispersant, grind resin or mixtures thereof;

0 to 80 wt % coloring pigment, extender pigment, anticorrosive pigment, other pigment types or mixtures thereof;

5 to 99.9 wt % water-borne, water-dispersible or water-soluble resin or mixtures thereof;

0 to 30 wt % slip additive, antimicrobial agent, processing aid, defoamer or mixtures thereof;

0 to 50 wt % coalescing or other solvents;

0.01 to 10 wt % surfactant, wetting agent, flow and leveling agents or mixtures thereof; and 0.01 to 5 wt % N,N-dialkyl urea.

15. An aqueous ink composition of 20 to 60 wt % components, which components comprise 1 to 50 wt % pigment;

0 to 50 wt % pigment dispersant, grind resin or mixtures thereof;

0 to 50 wt % clay base in a resin solution vehicle;

5 to 99 wt % water-borne, water-dispersible or water-soluble resin or mixtures thereof;

0 to 30 wt % coalescing solvent;

0.01 to 10 wt % processing aid, defoamer, solubilizing agent or mixtures thereof;

0.01 to 10 wt % surfactant, wetting agent or mixtures thereof; and 0.01 to 5 wt % N,N-dialkyl urea, the N,N-dialkyl urea being a compound of the structure

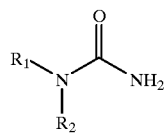

where $R_1$ and R2 are independently C1 to C6 alkyl or cycloalkyl, the sum of the carbon atoms in both $R_1$ and R2 being 6 to 12.

16. An aqueous agricultural composition of 0.1 to 80 wt % components, which components comprise

- 1 to 50 wt % pesticide, plant growth modifying agent or mixtures thereof;
- 0 to 5 wt % dye;
- 0 to 20 wt % thickener, stabilizer, co-surfactant, gel inhibitor, defoaming agent or mixtures thereof;
- 0 to 25 wt % antifreeze;
- 0 to 50 wt % coalescing or other solvents;
- 0.01 to 10 wt % surfactant; and
- 0.1 to 50 wt % N,N-dialkyl urea, the N,N-dialkyl urea being a compound of the structure

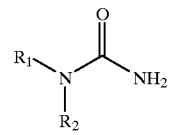

where $R_1$ and $R_2$ are independently C1 to C6 alkyl or cycloalkyl, the sum of the carbon atoms in both $R_1$ and $R_2$ being 6 to 12.

* * * * *